United States Patent [19]

Stults et al.

[11] Patent Number: 5,294,738
[45] Date of Patent: Mar. 15, 1994

[54] PROCESS FOR SELECTIVE HYDRODEFLUORINATION

[75] Inventors: Jeffrey S. Stults, Grand Island; Lawrence B. Fertel, Williamsville; William S. Derwin, Buffalo, all of N.Y.

[73] Assignee: Occidental Chemical Corporation, Niagara Falls, N.Y.

[21] Appl. No.: 863,264

[22] Filed: Apr. 3, 1992

[51] Int. Cl.$^5$ .............................................. C07C 51/06
[52] U.S. Cl. ................... 562/483; 548/476; 548/480; 562/480
[58] Field of Search ............... 548/476, 480; 562/480, 562/483

[56] References Cited

U.S. PATENT DOCUMENTS

| | | | |
|---|---|---|---|
| 4,769,493 | 9/1988 | Ito et al. | 562/480 |
| 4,925,966 | 5/1990 | Kobayashi et al. | 558/419 |
| 4,935,541 | 6/1990 | O'Reilly et al. | 562/479 |
| 4,981,999 | 1/1991 | O'Reilly et al. | 562/480 |
| 5,086,188 | 2/1992 | Fertel et al. | 562/483 X |

FOREIGN PATENT DOCUMENTS

| | | |
|---|---|---|
| 156656 | 3/1989 | Japan . |
| 1-160944 | 6/1989 | Japan . |
| 1-258639 | 10/1989 | Japan . |
| 2-115156 | 4/1990 | Japan . |
| 2-117643 | 5/1990 | Japan . |
| 1-169542 | 6/1990 | Japan . |

OTHER PUBLICATIONS

O'Reilly et al., *SYNLETT*, Jun. 1990; pp. 339–340.

*Primary Examiner*—Josá G. Dees
*Assistant Examiner*—Vera C. Clarke
*Attorney, Agent, or Firm*—Wayne A. Jones; Arthur S. Cookfair

[57] ABSTRACT

A process for the selective hydrodefluorination of a tetrafluorophthalimide compound of the formula

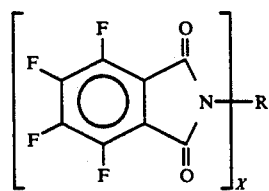

where X is 1 and R is a monovalent organo group; or X is 2 and R is a divalent organo group; comprises reacting (I) the tetrafluorophthalimide with zinc in an aqueous alkali metal hydroxide medium. The product may be hydrolyzed to form 3,4,6-trifluorophthalic acid.

22 Claims, No Drawings

PROCESS FOR SELECTIVE HYDRODEFLUORINATION

BACKGROUND OF THE INVENTION

1. Field of the Invention

This invention relates to a method for the selective hydrodefluorination of an N-substituted 3,4,5,6-tetrafluorophthalimide. The product may be hydrolyzed to form 3,4,6-trifluorophthalic acid, which, in turn, is a useful chemical intermediate for the synthesis of 2,4,5-trifluorobenzoic acid. The latter is a valuable chemical intermediate for the further preparation of quinolone antibacterials.

2. Prior Art

Various methods for the preparation of 2,4,5-trifluorobenzoic acid, or precursors thereof, are disclosed in the literature. O'Reilly, N. J.; Derwin, W. S.; and Lin, H. C.; SYNLETT, June 1990; 339; disclose the preparation of 3,4,6-trichlorophthalic acid by hydrodechlorination of 3,4,5,6-tetrachlorophthalic acid with zinc dust in aqueous sodium hydroxide.

U.S. Pat. No. 4,981,999 to O'Reilly, Derwin, and Lin discloses the preparation of 3,4,6-trichlorophthalic acid by hydrodechlorination of 3,4,5,6-tetrachlorophthalic acid or anhydride with a hydrodechlorinating metal, such as zinc, in the presence of a base, such as aqueous sodium hydroxide. The trichlorophthalic acid may then be converted to the corresponding trifluorobenzoic acid. The patentees provide comparative data showing that the subject process of selective dehalogenation using zinc dust and aqueous sodium hydroxide produce 3,4,6-trihalophthalic acid, is efficient for the conversion of tetrachlorophthalic anhydride to 3,4,6-trichlorophthalic acid (97.8% yield) and substantially ineffective for the conversion of tetrafluorophthalic acid to 3,4,6-trifluorophthalic acid (about 3% yield of desired product with about 96% of hydroxy-trifluoro-phthalic and -benzoic acids).

U.S. Pat. No. 4,935,541 to Nowak and Lin discloses the preparation of trifluorophthalic acid by preparation and fluorination of an alkyl or aryl trichlorophthalimide followed by hydrolysis to the trifluorophthalic acid.

U.S. Pat. No. 4,769,493 to Ito, Matsushita, Shimizu, and Ishikawa discloses a similar process involving fluorination of an organo-N-tetrachlorophthalimide to form the corresponding N-tetrafluorophthalimide and hydrolysis to the tetrafluorophthalic acid.

U.S. Pat. No. 4,925,966 discloses the reaction of a tetrafluoroisophthalonitrile with a metal hydride, such as sodium borohydride, to give 2,4,5-trifluoroisophthalonitrile.

Treatment of tetrafluorophthalonitrile with zinc in H$_2$SO$_4$ led to 3,4,6-trifluorophthalonitrile in an 88% yield (JP 01,160,944 (1988); CA 112:55243t). In a similar vein, 2,4,5,6-tetrafluoroisophthalonitrile was treated with zinc in aqueous sulfuric acid leading to 2,4,5-trifluoroisophthalonitrile (JP 01,258,639 (1989); CA 112:178350h); the same conversion was also reported using zinc in acetic acid solvent (JP 02,117,643 (1990); CA 113:131769g). Also, 3-chloro-2,4,6-trifluoroisophthalonitrile was converted to 3-chloro-2,6-difluoroisophthalonitrile using zinc in acetic acid solvent (JP 02,169,542; CA 113:190932c).

The conversion of pentafluorobenzonitrile to 2,3,5,6-tetrafluorobenzonitrile, by reaction with zinc in aqueous potassium dihydrogenphosphate is reported in Japanese Patent 02,115,156 (1990). A similar conversion using zinc in aqueous ethanol with added acetic acid is reported in Japanese Patent 01,56,656 (CA 112:7178d).

SUMMARY OF THE INVENTION

The present invention comprises a process for the selective hydrodefluorination of a tetrafluorophthalimide of the formula

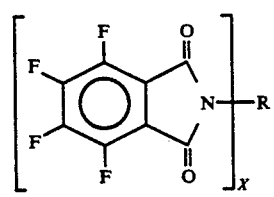

where X is 1 or 2 and, when X is 1, R is a monovalent organo group; and when X is 2, R is a divalent organo group; by reaction of the compound (I) with zinc in an aqueous alkali metal hydroxide medium.

Since the reaction occurs in an aqueous medium, some hydrolysis of the phthalimide is likely with a resultant formation of trifluorophthalic acid and/or intermediate trifluorophthalamic acid.

The hydrodefluorination occurs at the 4 or 5 position and the crude tri-fluoro product may be a mixture containing one or more of the following:

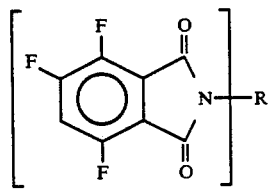

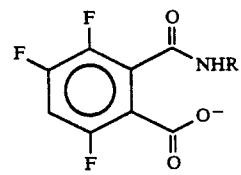

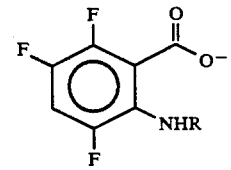

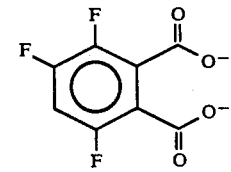

where X and R are as defined above.

Upon subsequent hydrolysis of the crude trifluoro product, the product is converted to the 3,4,6-trifluorophthalic acid.

DETAILED DESCRIPTION OF THE INVENTION

The fluorinated phthalimides (formula I, above) employed as reactants in the process of this invention, are conveniently prepared, in a known manner, by halogen exchange reaction of the corresponding tetra-chlorophthalimide with potassium fluoride. The tetrachlorophthalimides may be prepared, in a known manner, by condensation of tetrachlorophthalic anhydride with an appropriate amine or diamine in the required stoichiometry. The reaction may be conveniently carried out in a solvent such as acetic acid, or a dipolar aprotic solvent such as dioxane or sulfolane.

The selective defluorination reaction which forms the basis for this invention may be exemplified by the following equation:

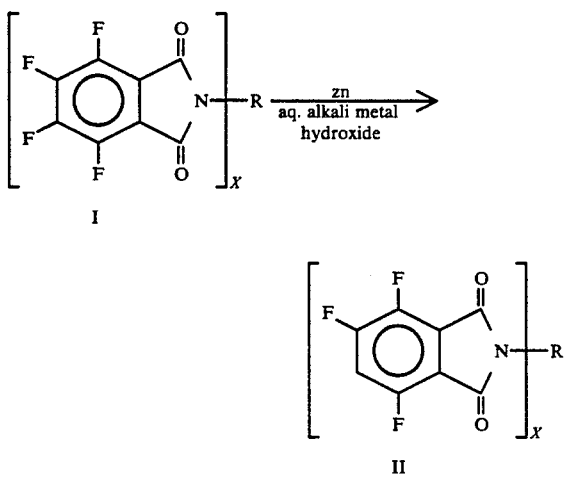

where X is 1 or 2. when X is 1, R is a monovalent organo group which may be an alkyl, cycloalkyl, alkenyl, cycloalkenyl or aryl group, unsubstituted or substituted (with substituents inert to the reaction medium). Preferred mono organo groups include, for example, alkyl, cycloalkyl, alkenyl, or cycloalkenyl of up to 8 carbon atoms and arylene of 6-14 carbon atoms. Most preferred monovalent organo groups are alkyl of 1-4 carbon atoms, phenyl, tolyl or xylyl. When X is 2, R is a divalent organo group which may be an alkylene, cycloalkylene, alkenylene, or cycloalkenylene, unsubstituted or substituted (with substituents inert to the reaction medium), preferably of up to 8 carbon atoms, or arylene, preferably of 6-14 carbon atoms. Most preferred divalent organo groups are alkylene of 2-6 carbon atoms, phenylene, toluidene, biphenyl, or diphenyl ether.

The reaction is carried out in an aqueous alkali metal hydroxide wherein the concentration of alkali metal hydroxide is typically from 1 to 50%. Suitable alkali metal hydroxides include NaOH, KOH and LiOH. A preferred reaction medium is 5-20% aqueous NaOH and most preferably 10% NaOH. The amount of NaOH employed should be at least sufficient to provide a molar ratio of NaOH:tetrafluorophthalimide (I) of 1:1. Higher amounts may be employed.

The zinc metal reactant may be added to the reaction medium in various available commercial forms, for example, as zinc mesh or zinc dust. The proportions of zinc employed in the reaction may vary from 1 to 6 or more equivalents per mole of fluorinated phthalimide reactant. Larger proportions of zinc may be employed but provide no added advantage. A preferred proportion is from about 2 to about 4 equivalents of zinc per mole or equivalent of the tetrafluorophthalimide.

The reaction temperature may vary considerably, but will typically be in the range of about room temperature (20° C.) to 80° C. Higher or lower temperatures may be employed but are generally less efficient. The preferred operating temperature is about 60° to 70° C. The reaction is carried out in the liquid phase, preferably at atmospheric pressure; however, superatmospheric pressure may be employed.

In addition to the aqueous solvent, various co-solvents which are chemically inert to the reactants present may be employed. Suitable co-solvents should be miscible with water, be a solvent for the fluorinated phthalimide reactant and be inert to the reaction medium. Typical co-solvents that may be employed are tetrahydrofuran, dioxane, and the like.

The reaction product of the selective hydrofluorination reaction may be conveniently hydrolyzed by further reaction with an aqueous base or a mineral acid to form 3,4,6-trifluorophthalic acid. Hydrolysis is preferably carried out by reaction with a mineral acid such as phosphoric acid, hydrochloric acid or, most preferably, sulfuric acid.

The following specific examples are provided to further illustrate the invention and the manner in which it may be carried out. The specific details given in the examples have been chosen for purposes of illustration and are not to be construed as limiting of the invention. In the examples, unless otherwise indicated, all temperatures are in degrees Celsius.

EXAMPLE 1

A mixture of tetrafluoro-N-methylphthalimide (66.93 g, 0.29 mol), zinc dust (75.13 g, 1.15 mol) and 500 mL of 10% sodium hydroxide was heated at 70° C. for 2 hours, at which time analysis (GC) showed complete consumption of the starting material. The reaction was cooled and the zinc salts were filtered off. The filtrate was acidified with concentrated HCl to a pH of 1 and stirred for 0.5 hours. The organics were extracted into ethyl acetate, and the ethyl acetate layer washed with water and dried over MgSO4. Removal of the solvent left 58.56 g of solid material which, by GC and $^{19}F$ NMR was found to contain 76% of trifluorophthalamic acid and 15% 3,4,6-trifluorophthalic acid. The mixture was hydrolyzed by mixing with 150 mL of 50% sulfuric acid and heating at 160° C. for 6 hours, then washed with water, extracted with ethyl acetate and dried to yield 54.9 g of 3,4,6-trifluorophthalic acid, the identification of which was confirmed by comparison of GC retention times and $^{19}F$ NMR chemical shifts to a known sample.

EXAMPLE 2

Effect of Reaction Variables: Sodium Hydroxide

A series of experiments were run following the general procedure of Example 1, except that the concentration of the aqueous sodium hydroxide was varied as shown. In all experiments, 1.0 g of tetrafluoro-N-methylphthalimide, 5 mL of NaOH solution and 2 equivalents of zinc were used. The reactions were carried out at about 60° C.

| Example | Concentration of NaOH | Conversion to Product |
| --- | --- | --- |
| 2A | 5% | 30% |
| 2B | 10% | 91% |
| 2C | 15% | 69% |
| 2D | 20% | 77% |

In the table, the conversion to product is the area percent on the GC containing the trifluorophthalamic acid and the trifluorophthalic acid.

EXAMPLE 3

Effect of Reaction Variables: Zinc

In this series of experiments, the general procedure of Example 2B was followed except that the amount of zinc was varied. In all the experiments, 2.5 mL of 10% NaOH and 0.5 g of tetrafluoro-N-methylphthalimide were used. The reactions were all run at room temperature.

| Example | Equivalents of Zn Added | Conversion to Product |
| --- | --- | --- |
| 3A | 1 | 22% |
| 3B | 2 | 38% |
| 3C | 3 | 72% |
| 3D | 4 | 91% |

EXAMPLE 4

Effect of Reaction Variables: Temperature

A series of reactions were run under conditions identical to Examples 3A-D, except that the reaction temperature was maintained at 60° C. throughout.

| Example | Equivalents of Zn Added | Conversion to Product |
| --- | --- | --- |
| 4A | 1 | 63% |
| 4B | 2 | 88% |
| 4C | 3 | 93% |
| 4D | 4 | 94% |
| 4E | 6 | 97% |

EXAMPLE 5

Use of a Co-solvent

A mixture of tetrafluoro-N-methylphthalimide (1.0 g), zinc dust (1.1 g), tetrahydrofuran (5 mL) and 20% aqueous sodium hydroxide (2 mL) was heated to 60° C. for 24 hours, at which time a reaction assay showed the major products to be trifluorophthalamic acid and trifluorophthalic acid as described in Example 1.

EXAMPLE 6

A mixture of tetrafluoro-N-phenylphthalimide (22.15 g) and zinc dust (29 g), in 10% aqueous sodium hydroxide (165 mL) was heated to 69° C. and maintained thereat, with stirring, for 5 hours. Analysis of the reaction product by GC indicated a mixture of 3,4,6-trifluorophthalic acid and 3,4,6-trifluoro-N-phenylphthalimide.

EXAMPLE 7

A) Preparation of N,N'-dimethylenebis(tetrafluorophthalimide)

A mixture of N,N'-dimethylenebis(tetrachlorophthalimide) (50 g) (prepared by reaction of ethylene diamine and phthalic anhydride) and anhydrous potassium fluoride (48.5 g) in 450 mL of dry sulfolane, was heated at 200° C. and maintained thereat, with stirring, for 4 hours. The reaction mixture was then cooled, the salts removed by filtration, and the filtrate poured into 1.5 L of water. The product was filtered and sublimed (225° C. at 0.025 mm Hg) to yield 17.65 g of N,N'-dimethylenebis(tetrafluorophthalimide) as a yellow solid. The material was slurried in dichloromethane, filtered and dried to yield 15.5 g of pure product.

B) Hydrodefluorination

A mixture of N,N'-dimethylenebis(tetrafluorophthalimide) (1.0 g) and zinc dust (1.12 g), in 10% aqueous sodium hydroxide (5 mL), was heated to 65° C. and maintained thereat for 9 hours, then cooled to room temperature and filtered to remove zinc salts. Analysis of the filtrate by GCMS showed a structure consistent with that of N,N'-dimethylenebis(3,4,6-trifluorophthalimide). The filtrate was directly acidified by addition of concentrated sulfuric acid (12.8 g) and heated at 150° C. for 3 hours. Analysis of the final reaction mixture by GC and $^{19}$F NMR indicated 55% 3,4,6-trifluorophthalic acid.

The following examples, 8C–11C, are presented for purposes of comparison with various prior art processes:

EXAMPLE 8C

Tetrafluoro-N-methylphthalimide (1.0 g), zinc dust (1.0 g) and glacial acetic acid (10 mL) were charged together and stirred at room temperature. Analysis of the reaction mixture after 10 hours, showed the product to be N-methyl-3-hydroxy-3,4,5,6-tetrafluoro-i-isoindolinone.

EXAMPLE 9C

Tetrafluoro-N-methylphthalimide (1.0 g), sodium borohydride (0.1 g), isopropyl alcohol (100 mL) were combined and stirred at room temperature for 8 hours. Analysis of the product showed it to be identical to that in Example 8C.

EXAMPLE 10C

Tetrafluorophthalic acid (0.5 g), zinc dust (0.36 g) and 5 mL of 20% aqueous sodium hydroxide were combined and heated at 100° C. for 24 hours, at which time analysis of the mixture showed the major product to be 3-hydroxy-2,4,5-trifluorobenzoic acid.

EXAMPLE 11C

Tetrafluorophthalonitrile (5.0 g), zinc dust (6.54 g) and 25 mL of 10% aqueous sodium hydroxide were mixed together and heated at 72° C. for 3 hours. Analysis of the reaction mixture failed to detect any defluorinated materials.

What is claimed is:

1. A process for the preparation of 3,4,6-trifluorophthalic acid of the formula

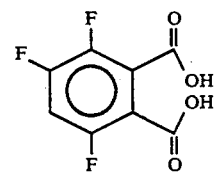

which comprises
(A) treating tetrafluorophthalimide of the formula

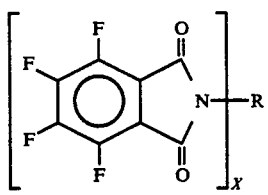

where X is 1 or 2; and when X is 1, R is a monovalent organo group; and when X is 2, R is a divalent organo group, with zinc in the presence of aqueous alkali metal hydroxide to form a selectively defluorinated reaction product, and
(B) hydrolyzing the reaction product.

2. A process according to claim 1 wherein X is 1.
3. A process according to claim 2 wherein R is alkyl.
4. A process according to claim 3 wherein R is methyl and the aqueous alkali metal hydroxide is 1-50% aqueous sodium hydroxide.
5. A process according to claim 2 wherein R is aryl.
6. A process according to claim 5 wherein R is phenyl and the aqueous alkali metal hydroxide is 1-50% aqueous Sodium hydroxide.
7. A process according to claim 1 wherein X is 2.
8. A process according to claim 7 wherein R is methylene and the aqueous alkali metal hydroxide is 1-50% aqueous sodium hydroxide.
9. A process for the selective hydrodefluorination of a tetrafluorophthalimide compound of the formula

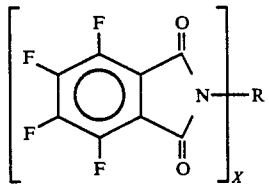

where X is 1 or 2; and when X is 1, R is a monovalent organo group; and when X is 2, R is a divalent organo group; which comprises reacting the compound (I) with zinc in an aqueous alkali metal hydroxide medium.

10. A process according to claim 9 wherein X is 1.
11. A process according to claim 10 wherein R is alkyl.
12. A process according to claim 11 wherein R is methyl and the aqueousalkali metal hydroxide is 1-50% aqueous sodium hydroxide.
13. A process according to claim 12 wherein the aqueous sodium hydroxide medium is 5-20% aqueous sodium hydroxide.
14. A process according to claim 10 carried out in the presence of a water-miscible co-solvent.
15. A process according to claim 14 wherein the co-solvent is tetrahydrofuran.
16. A process according to claim 10 wherein R is aryl.
17. A process according to claim 10 wherein R is phenyl and the aqueous alkali metal hydroxide is 1-50% aqueous sodium hydroxide.
18. A process according to claim 17 wherein the aqueous sodium hydroxide medium is 5-20% aqueous sodium hydroxide.
19. A process according to claim 9 wherein X is 2.
20. A process according to claim 19 wherein R is methylene.
21. A process according to claim 20 wherein the aqueous alkali metal hydroxide medium is 1-50% aqueous sodium hydroxide.
22. A process for the preparation of 3,4,6-trifluorophthalic acid of the formula

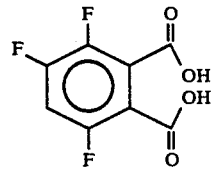

which comprises
(A) treating tetrafluorophthalimide of the formula

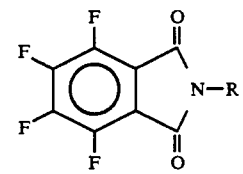

where R is alkyl of 1-8 carbon atoms or aryl of 6-14 carbon atoms, with zinc in the presence of 5-20% aqueous sodium hydroxide at a temperature of about 20° to 80° Celsius, to form a selectively defluorinated reaction product, and
(B) hydrolyzing the reaction product by treatment with a mineral acid.

* * * * *